United States Patent [19]

Ducret et al.

[11] 4,188,381
[45] Feb. 12, 1980

[54] FUNGICIDES HYDRAZINIUM PHOSPHITES

[75] Inventors: Jacques Ducret, Lyons; Jean-Michel Gaulliard, Orlienas; Jean Vial, Dardilly, all of France

[73] Assignee: Philagro, France

[21] Appl. No.: 872,435

[22] Filed: Jan. 26, 1978

[30] Foreign Application Priority Data

Feb. 14, 1977 [FR] France .................................. 77 04981

[51] Int. Cl.² .............................................. A01N 9/36
[52] U.S. Cl. .................................... 424/199; 260/569; 260/923
[58] Field of Search .................. 260/923, 569; 424/199

[56] References Cited

U.S. PATENT DOCUMENTS

| 2,773,796 | 12/1956 | Hackmann et al. | 424/128 OR |
| 2,850,425 | 9/1958 | Gaertner | 260/569 X |
| 4,075,324 | 2/1978 | Thizy et al. | 424/199 X |

FOREIGN PATENT DOCUMENTS 2456627 6/1975 Fed. Rep. of Germany .

Primary Examiner—Anton H. Sutto
Attorney, Agent, or Firm—Robert E. Burns; Emmanuel J. Lobato; Bruce L. Adams

[57] ABSTRACT

New derivatives of hydrazinium phosphites, their preparation and fungicidal compositions in which they are present are described. The new fungicidal derivatives have the formula

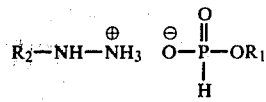

in which $R_1=H$, or an alkyl radical containing from 1 to 4 carbon atoms, and $R_2=H$, or a phenyl nucleus which is optionally substituted by one or more of the following atoms or radicals: halogen, alkyl radicals, containing from 1 to 4 carbon atoms, and the nitro radical; however, it is not possible for $R_1$ and $R_2$ to simultaneously represent a hydrogen atom. These products can be used in agriculture for combating fungal diseases in plants.

12 Claims, No Drawings

FUNGICIDES HYDRAZINIUM PHOSPHITES

BACKGROUND OF THE INVENTION

The present invention relates to new derivatives of hydrazinium phosphites, their preparation and the fungicidal compositions in which at least one of these compounds is present as the active material. Hydrazinium phosphites are sometimes called hydrazinium phosphonates.

More precisely, the invention relates to compounds corresponding to the formula:

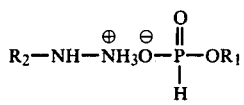

Formula 1 in which $R_1$ represents a hydrogen atom, or an alkyl radical containing from 1 to 4 carbon atoms, and $R_2$ represents a hydrogen atom, or a phenyl nucleus which is optionally substituted by one or more of the following atoms or radicals: the nitro radical, an alkyl radical ($C_1$-$C_4$) and halogen, it is not possible for $R_1$ and $R_2$ to simultaneously represent a hydrogen atom.

It has long been known that hydrazine (or hydrazine hydrate) exhibits valuable pesticidal properties, in particular fungicidal, bactericidal and insecticidal properties. Unfortunately, both hydrazine and hydrazine hydrate exhibit extremely high phytotoxicity, which completely prohibits their use for the treatment of plants.

In order to reduce this phytotoxicity, a process of fungicidal treatment using hydrazine salts with inorganic phosphorus acids chosen from the group comprising phosphoric acid, phosphorous acid, hypophosphoric acid and pyrophosphoric acid has been proposed in U.S. Pat. No. 2,773,796. This patent describes, in particular, the use of hydrazinium phosphite against tomato mildew (*Phytophthora infestans*) and against septoriosis in celery (*Septoria graveolentis*). However, no information is given concerning the possible use of this hydrazinium phosphite for the treatment of vine mildew (*Plasmopara viticola*); although, from an economic point of view, it is in fact vines which constitute one of the main fields of application of anti-mildew treatments. Experiments which we have carried out on vines in a greenhouse have shown that, when applied to the foliage, hydrazinium phosphite exhibits significant phytotoxicity towards vine seedlings, and that therefore it is not possible to use it in this field.

Furthermore, the use of compositions containing, as the active material, various derivatives of phosphorous acid has been proposed for fungicidal treatments.

Thus, the use, of inorganic or organic salts of phosphorous acid, as fungicides has been claimed in French Pat. No. 2,252,056 and; in its Certificate of Addition 2,285,812, the use of salts of phosphorous acid and of imidazole, cyclohexylamine or morpholine as fungicides has been claimed.

As organic salts of phosphorous acid, these two patents describe, in particular, acid phosphites of ammonium or of ammonium which is substituted by one or more alkyl, hydroxyalkyl or phenyl groups, this group itself being optionally substituted. However, no hydrazinium phosphite is described in the examples.

Furthermore, in French Pat. No. 2,254,276 the use has been claimed, of fungicides which are phosphonic acid monoesters (also called phosphites) of the general formula:

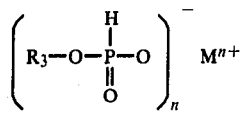

Formula 2 in which M represents a hydrogen atom, an optionally substituted ammonium cation, or a metal cation, n is an integer equal to the valency of M and $R_3$ can represent an alkyl radical containing from 1 to 18 carbon atoms. In its Certificate of Addition U.S. Pat. No. 2,288,463 the use of, fungicides is claimed, which are compounds of the formula 2 in which M is an ammonium cation which is substituted by one or more alkyl or hydroxyalkyl radicals, n is an integer ranging from 1 to 3 and $R_3$ can represent a $C_1$-$C_8$ alkyl group. This French Pat. No. 2,254,276 and its Certificate of Addition U.S. Pat. No. 2,288,463 describe, in particular, the use of ammonium alkyl-phosphites in which the ammonium ion is substituted by one or more alkyl, hydroxyalkyl or phenyl groups. However, no hydrazinium alkyl-phosphite is mentioned in the examples.

The phosphites or alkyl-phosphites described in these French Pat. Nos. 2,252,056 and 2,254,276, and in their respective Certificates of Addition U.S. Pat. Nos. 2,285,812 and 2,288,463, exhibit remarkable fungicidal properties, especially against vine mildew, namely an immediate, preventive or curative and systemic action combined, for the majority of the compounds, with the absence of phytotoxicity in vines. However, complementary experiments carried out on vines in the open air have shown that, depending on the climatic conditions, optionally substituted ammonium alkyl-phosphites can lead to significant occurrences of phytotoxicity in the vines, and that their use in this field is therefore to be proscribed.

Because of the well known phytotoxicity of hydrazine, and because of the results already observed on vines in the case of hydrazinium phosphite described in U.S. Pat. No. 2,773,796, and in the case of the above-mentioned phosphites or alkyl-phosphites of ammonium or of substituted ammonium, it could be expected that phosphites or alkyl-phosphites of hydrazinium or of substituted hydrazinium would generally exhibit high phytotoxicity, which would prohibit, in particular, their use by application to foliage.

SUMMARY OF THE INVENTION

It has now been found that, at the normal use doses, certain hydrazinium salts and phosphorous acid salts unexpectedly exhibit both good anti-fungal activity and the absence of phytotoxicity especially in vines.

It has also been found that the compounds of the general formula 1, in which $R_1$ represents an alkyl radical ($C_1$-$C_4$) and $R_2$ represents a hydrogen atom, exhibit essentially the same fungicidal activity as the best products in the abovementioned French patents and certificates of addition; however, unexpectedly, they do not cause any significant occurrence of phytotoxicity in vines.

Furthermore, this work has shown that the products of the general formula 1, in which $R_1$ represents a hydrogen atom or an alkyl radical ($C_1$-$C_4$), and $R_2$ represents a phenyl radical which is optionally substituted by one or more of the following atoms or radicals: nitro, alkyl ($C_1$-$C_4$) and halogen, exhibit satisfactory fungicidal properties and, in particular, that they exhibit a specific anti-fungal activity against piriculariosis in rice (*Piricularia oryzae*).

DESCRIPTION OF THE INVENTION

By way of comparison, both hydrazinium phosphite and the main compounds described in the abovementioned French patents or certificates of addition do not exhibit any significant anti-fungal activity with respect to this fungus at their normal use doses.

The compounds according to the invention are prepared in accordance with a process, which is in itself known, of reacting optionally substituted hydrazine hydrate with phosphorous acid or with a O,O-dialkyl phosphonate, in accordance with the following equation:

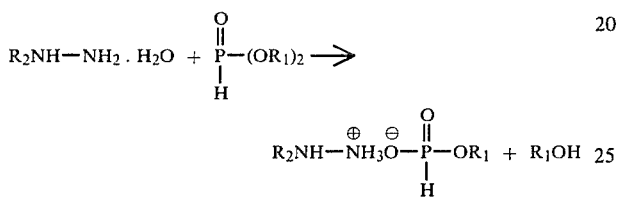

The reaction takes place spontaneously at ordinary temperature. It can be carried out either in an inert organic solvent medium, for example in ethanol, or without using a solvent. In certain cases, it can be advantageous to heat the reaction mixture in order to accelerate the reaction. In practice, temperatures of 15° to 120° C. give good results.

The following examples illustrate, by way of indication, the preparation of the compounds according to the invention, as well as the anti-fungal activity of these compounds.

EXAMPLE 1

Preparation of hydrazinium ethyl-phosphite of the general formula:

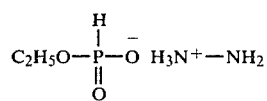

(compound No. 1)

0.2 mol of hydrazine hydrate is run, whilst stirring, into 0.2 mol of diethyl phosphite. During the addition, the mixture is heterogeneous and its temperature rises to 70° C. Ten minutes after the end of the addition, the mixture becomes homogeneous. The mixture is stirred for two hours, and the alcohol and water are then driven off in vacuo at 80° C. A clear oil remains.

Weight: 28.5 g
$n_D^{20}$: 1.4585
Yield: 100%

The structures were characterised by NMR carried out in $D_2O$.

| Percentage composition for $C_2H_{11}NO_3P$ | | | |
|---|---|---|---|
| | C % | H % | N % | P % |
| Calculated | 16.90 | 7.75 | 19.72 | 21.83 |
| Found | 16.52 | 8.16 | 18.81 | 21.50 |

EXAMPLE 2

Using suitable starting materials, the following compounds were prepared by following the procedure of Example 1:

| Compound No. | $R_1$ | $R_2$ | Melting point | Percentage analysis | |
|---|---|---|---|---|---|
| | | | | % Calculated | Found |
| 2 | H— |  | 116.7° C. | C 37.89 | 36.59 |
| | | | | H 5.79 | 6.07 |
| | | | | N 14.74 | 14.55 |
| | | | | P 16.32 | 16.15 |
| 3 | H— | —$NO_2$ | 154° C. | C 30.64 | 30.84 |
| | | | | H 4.26 | 4.31 |
| | | | | N 17.87 | 18.31 |
| | | | | P 13.19 | 12.90 |
| 4 | $CH_3$— |  | 138° C. | C 41.18 | 41.04 |
| | | | | H 6.37 | 6.36 |
| | | | | N 13.73 | 13.79 |
| | | | | P 15.20 | 14.65 |
| 5 | $C_2H_5$— |  | 113° C. | C 44.03 | 43.11 |
| | | | | H 6.88 | 6.45 |
| | | | | N 12.84 | 12.55 |
| | | | | P 14.22 | 13.87 |

EXAMPLE 3

In vitro test on fungistatic action.

The action of the compounds according to the invention on the development of the following fungi is studied: *Piricularia oryzae*, responsible for piriculariosis in rice, *Botrytis cinerea*, responsible for grey rot in vines *Colletotrichum lagenarium*, responsible for anthracnosis in Cucurbitaceae.

Each experiment is carried out in the following manner: 5 ml of gelose (malt/agar medium) are placed in test tubes, and each tube is then stoppered and sterilized for 20 minutes at 120° C. The tubes are then placed in a water bath kept at 60° C.

A determined amount of a 1% strength acetone solution of the compound to be tested is then injected, by means of a pipette, into each tube, in order to obtain a determined concentration, in the culture, of the compound to be tested.

After 24 hours, the tubes are inoculated either by the injection, using a syringe, of 0.5 ml of a suspension of spores containing 100,000 spores/$cm^3$, or by a mycelian implant having a diameter of 8 mm. As a reference, a tube is taken which is analogous to that above, but in which the gelose medium does not contain any active material. After 9 days at 26° C., in the dark, the surface of the inhibition zone observed is evaluated, for a given concentration of active material, and expressed as a percentage relative to the surface inoculated.

In the table below, the weakest doses which make it possible to produce a 100% inhibition of the development of the fungus in question are indicated in g/liter, on the one hand in the case of the compounds 2 to 5 according to the invention, and on the other hand in the case of two comparison compounds which are:

A: hydrazinium phosphite described in U.S. Pat. No. 2,773,796, and

B: aluminum ethyl-phosphite described on page 17 of French Pat. No. 2,288,463.

Measurements were carried out for doses of active material ranging from 0.01 to 0.2 g/liter. The indication >0.2 signifies that the product is inactive at 0.2 g/liter.

| Compound No. | Piricularia oryzae | Botrytis cinerea | Colletotrichum lagenarium |
|---|---|---|---|
| 2 | 0.05 | 0.2 | 0.2 |
| 3 | 0.05 | 0.15 | 0.2 |
| 4 | 0.05 | 0.1 | 0.1 |
| 5 | 0.05 | 0.1 | 0.15 |
| Comparison A-hydrazinium phosphite | >0.2 | >0.2 | >0.2 |
| Comparison B-aluminum ethyl-phosphite | >0.2 | >0.2 | >0.2 |

EXAMPLE 4

In vitro test on *Plasmopara viticola* in seedlings (preventive treatment).

Vine seedlings (Gamay variety), which have been cultivated in pots, are treated by spraying, using a gun, onto the underside of the leaves, an aqueous suspension of a wettable powder having the following composition by weight:

active material to be tested ... 20%
deflocculant (calcium lignosulphate) ... 5%
wetting agent (sodium alkylarylsulphonate) ... 1%
filler (aluminum silicate) ... 74% the suspension having the desired dilution and containing the active material to be tested at the dose in question; each test is repeated three times.

After 48 hours, contamination is carried out by spraying; onto the underside of the leaves, an aqueous suspension containing about 80,000 units/cm$^3$ of fungus spores.

The pots are then placed for 48 hours in an incubating cell at 100% relative humidity and at 20° C.

The seedlings are checked 9 days after infestation. Under these conditions, it is observed that, at a dose of 0.5 g/liter, the compound of Example 1 provides total protection, without showing any phytotoxicity.

EXAMPLE 5

In vivo test on Piricularia oryzae in rice seedlings.

The same method is used as in Example 4, but treating both sides of the leaves of the rice seedlings (and not simply the underside as in the preceding example).

Under these conditions, it is observed that, at a dose of 0.5 g/liter, compounds Nos. 2, 3 and 5 provide good protection. At this dose, no occurrence of phytotoxicity in the rice seedlings was noted.

EXAMPLE 6

In vivo test on ground fungus.

The action of compound No. 3 on Pythium de Baryanum in the "Small Green Paris" variety of gherkin is shaded.

Each experiment is carried out in the following manner: a medium containing a fungus culture is mixed with sterilized earth, and pots are filled with this mixture. The earth is infested after 8 days. It is then treated by watering with a suspension, having various concentrations, of the material to be tested. The latter consists of a wettable powder prepared as in Example 4. Gherkin seeds are then sown in the treated ground.

15 days after sowing, assessment is carried out in accordance with the number of destroyed or diseased plants, relative to an untreated reference and an uncontaminated reference.

Under these conditions, it is observed that, at a dose of 0.5 g/liter, compound No. 3 provides good protection, and that at a dose of 1 g/liter, it provides total protection. No occurrence of phytotoxicity was observed at this dose.

EXAMPLE 7

In vivo test, by absorption through the roots, of systemic action on vine mildew.

Several vines (Gamay variety), each being in a pot containing vermiculite and a nutrient solution, are watered at the base with 40 cm$^3$ of a solution containing 0.5 g/liter of the material to be tested. After two days, the vine is contaminated with an aqueous suspension containing 100,000 spores/cm$^3$ of *Plasmopara viticola*. Incubation is allowed to proceed for 48 hours in a chamber at 20° C. and at a relative humidity of 100%. The degree of infestation, relative to an infested reference plant which has been watered with 40 cm$^3$ of distilled water, is observed after about 9 days.

Under these conditions, it is observed that, when absorbed through the roots, compound 1 provides total protection of the vine leaves against mildew, which clearly demonstrates the systemic character of this compound.

EXAMPLE 8

Open air test on vine mildew.

Groups of vine-stocks (Gamay variety), planted two years previously, are naturally infested on 25th May and again on 19th July, following abundant rain and daily watering. These groups of stocks are then treated every 12 days from 16th May to 18th August with an aqueous solution of compound 1 containing 200 g/hl of active material.

At the end of the treatment, the ratio in % of the number of leaves contaminated by mildew in the treated sample to the number of leaves contaminated by mildew in the untreated sample was 6.1%.

Eight days after the end of the treatment, the percentage of mildew on the fresh growth was, respectively, 1.7% in the case of the treated samples and 32% in the case of the untreated reference samples.

Examples 1, 7 and 8 clearly show the remarkable anti-mildew activity of hydrazinium ethyl-phosphite, the compound of Example 1, this activity being effective both for preventing and for stopping the development of the fungus. The hydrazinium alkyl-phosphites according to the invention can be used, both in preventive and in curative treatment, for the protection of plants against the fungal diseases caused, for example, by phycomycetes and ascomycetes, and especially for the protection of plants such as, in particular, vine, hop or tobacco plants, against mildews of the *Plasmopara viticola, Peronospora tabacii* or *Pseudoperonospora humuli* type.

Phenylhydrazinium phosphites, which are optionally substituted on the phenyl nucleus, are preferably used for the treatment of the fungal diseases caused by Piricularia oryzae. They can also be used against other fungal diseases such as those caused by *Botrytis cinerea, Colletotrichum lagenarium* and *Pythium de Baryanum*.

The use doses can vary within wide limits depending on the virulence of the fungus and on the climatic conditions.

In general terms, doses containing 0.1 to 3 g/liter of active material are very suitable.

For use in practice, the compounds according to the invention are rarely employed by themselves. Most frequently, they form part of compositions which generally comprise a carrier and/or a surface-active agent in addition to the active material according to the invention.

The term "carrier", for the purpose of the present description, denotes an organic or inorganic, natural or synthetic material with which the active material is combined in order to facilitate its application to the plant, to the seed or to the ground, or in order to facilitate its transport or handling. The carrier can be solid (clays, natural or synthetic silicates, resins, waxes, solid fertilisers or the like) or fluid (water, alcohols, ketones, petroleum fractions, chlorinated hydrocarbons or liquefied gases).

The surface-active agent can be an emulsifier, dispersing agent or wetting agent and can be ionic or non-ionic. Examples which may be mentioned are salts of polyacrylic acids and of ligninsulphonic acids, and condensates of ethylene oxide with fatty alcohols, fatty acids or fatty amines.

The compositions according to the invention can be prepared in the form of wettable powders, soluble powders, powders for dusting, granules, solutions, in particular aqueous solutions, emulsifiable concentrates, emulsions, suspension concentrates and aerosols.

The wettable powders are usually prepared so that they contain from 20 to 95% by weight of active material, and they usually contain, in addition to a solid carrier, from 0 to 5% by weight of a wetting agent, from 3 to 10% by weight of a dispersing agent and, where necessary, from 0 to 10% by weight of one or more stabilizers and/or other additives such as penetrating agents, adhesives or anti-caking agents, dyestuffs and the like.

By way of example, the composition of a wettable powder is given:

| | |
|---|---:|
| active material | 50% |
| calcium lignosulphate (deflocculant) | 5% |
| anionic wetting agent (alkylarylsulphonate) | 1% |
| anti-caking silica | 5% |
| kaolin (filler) | 39% |

The water-soluble powders are obtained in the customary manner by mixing from 20 to 95% by weight of the active material and from 0 to 10% of an anti-caking filler, the remainder consisting of a water-soluble solid carrier, especially a salt.

An example of the composition of a soluble powder is given:

| | |
|---|---:|
| active material | 70% |
| anionic wetting agent | 0.5% |
| anti-caking silica | 5% |
| sodium sulphate (solid carrier) | 24.5% |

Aqueous dispersions and aqueous emulsions, for example compositions obtained by diluting a wettable powder or an emulsifiable concentrate, according to the invention, with water, are included in the general scope of the present invention. These emulsions can be of the water-in-oil type or of the oil-in-water type, and they can have a thick consistency, such as that of a "mayonnaise".

The compositions according to the invention can contain other ingredients, for example protective colloids, adhesives or thickeners, thixotropic agents, stabilizers or sequestering agents, as well as other known active materials having pesticidal properties, in particular acaricidal or insecticidal properties.

We claim:

1. A process for the treatment of crops against fungal diseases, which comprises applying to a crop a fungicidal composition containing as active material at least one compound of the formula

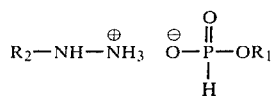

in which $R_1$ represents a hydrogen atom, or an alkyl radical containing from 1 to 4 carbon atoms, and $R_2$ represents a hydrogen atom, or a phenyl nucleus which is optionally substituted by one or more of the following atoms or radicals: halogen, alkyl radicals containing from 1 to 4 carbon atoms, and the nitro radical, provided that $R_1$ and $R_2$ do not simultaneously represent a hydrogen atom at a dose of between 10 g/hl and 300 g/hl.

2. A process of treating crops according to claim 1, in which vines are treated against mildew, and in which said composition contains as active material a compound of the formula

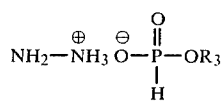

in which $R_3$ represents an alkyl group containing from 1 to 4 carbon atoms.

3. A process of treating crops according to claim 1, in which said treatment is against piriculariosis in rice, and in which said composition contains as active material a compound of the formula

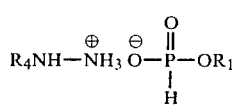

in which $R_1$ has the same meaning as in claim 1, and $R_4$ represents a phenyl nucleus which is optionally substituted by a nitro radical.

4. A derivative of hydrazinium phosphite, of the formula:

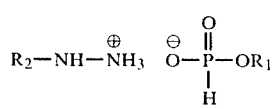

in which $R_1$ represents a hydrogen atom, or an alkyl radical containing from 1 to 4 carbon atoms, and $R_2$ represents a hydrogen atom, or a phenyl nucleus which is optionally substituted by one or more of the following atoms or radicals: halogen, alkyl radicals containing from 1 to 4 carbon atoms, and the nitro radical, provided that $R_1$ and $R_2$ do not simultaneously represent a hydrogen atom.

5. A derivative of hydrazinium phosphite according to claim 4 in which said derivative has the formula

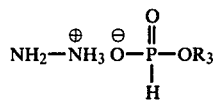

in which $R_3$ represents an alkyl group containing from 1 to 4 carbon atoms.

6. A derivative of hydrazinium phosphite according to claim 4 in which said derivative has the formula

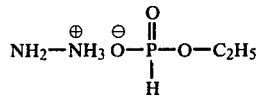

7. A derivative of hydrazinium phosphite according to claim 4 in which said derivative has the formula

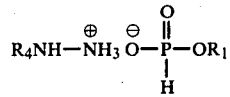

in which $R_1$ has the same meaning as in claim 4, and $R_4$ represents a phenyl nucleus which is optionally substituted by a nitro radical.

8. A fungicidal composition for combating fungal diseases in plants, which contains, as the active material, at least one compound according to claim 1.

9. A composition according to claim 8, which contains from 20 to 95% by weight of said active material in combination with and at least one member of the group consisting of an agriculturally acceptable carrier and an agriculturally acceptable surface active agent.

10. A composition according to claim 8, in which said active material is chosen from amongst the compounds of the formula:

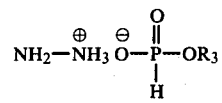

in which $R_3$ represents an alkyl group containing from 1 to 4 carbon atoms.

11. A composition according to claim 10, in which said the active material is the compound of the general formula:

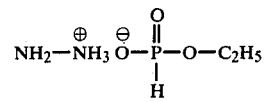

12. A composition according to claim 8, in which the active material is chosen from amongst the compounds of the formula:

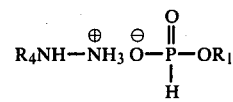

in which $R_1$ has the same meaning as in claim 1, and $R_4$ represents a phenyl nucleus which is optionally substituted by a nitro radical.

* * * * *